United States Patent
Qiang et al.

(10) Patent No.: US 10,314,527 B2
(45) Date of Patent: *Jun. 11, 2019

(54) SENSORS FOR ANALYTE DETECTION AND METHODS OF MANUFACTURE THEREOF

(71) Applicant: University of Connecticut, Farmington, CT (US)

(72) Inventors: Liangliang Qiang, Willimantic, CT (US); Santhisagar Vaddiraju, Willimantic, CT (US); Fotios Papadimitrakopoulos, West Hartford, CT (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 300 days.

This patent is subject to a terminal disclaimer.

(21) Appl. No.: 15/226,150

(22) Filed: Aug. 2, 2016

(65) Prior Publication Data

US 2017/0156652 A1   Jun. 8, 2017

Related U.S. Application Data

(62) Division of application No. 13/164,656, filed on Jun. 20, 2011, now Pat. No. 9,402,574.

(Continued)

(51) Int. Cl.
*A61B 5/145* (2006.01)
*A61B 5/1473* (2006.01)
(Continued)

(52) U.S. Cl.
CPC ........ *A61B 5/14865* (2013.01); *A61B 5/1473* (2013.01); *A61B 5/1495* (2013.01);
(Continued)

(58) Field of Classification Search
USPC .................................. 205/661; 204/400–412
See application file for complete search history.

(56) References Cited

U.S. PATENT DOCUMENTS

| | | |
|---|---|---|
| 4,357,750 A | 11/1982 | Ostman |
| 6,863,753 B1 | 3/2005 | Murooka et al. |

(Continued)

OTHER PUBLICATIONS

Errachid, A.; Ivorra, A.; Aguilo, J.; Villa, R.; Zine, N.; Bausells, J., "New technology for multi-sensor silicon needles for biomedical applications" Sensors and Actuators, B: Chemical 2001, 78, (1-3), 279-284.

(Continued)

*Primary Examiner* — Christian Jang
*Assistant Examiner* — Mitchell E Alter
(74) *Attorney, Agent, or Firm* — Cantor Colburn LLP

(57) ABSTRACT

Disclosed herein is a sensor comprising a conduit; the conduit comprising an organic polymer; a working electrode; the working electrode being etched and decorated with a nanostructured material; a reference electrode; and a counter electrode; the working electrode, the reference electrode and the counter electrode being disposed in the conduit; the working electrode, the reference electrode and the counter electrode being separated from each other by an electrically insulating material; and wherein a cross-sectional area of the conduit that comprises a section of the working electrode, a section of the reference electrode and a section of the counter electrode is exposed to detect analytes.

11 Claims, 11 Drawing Sheets

Related U.S. Application Data

(60) Provisional application No. 61/398,498, filed on Jun. 25, 2010.

(51) Int. Cl.
  *A61B 5/1486* (2006.01)
  *A61B 5/1495* (2006.01)

(52) U.S. Cl.
  CPC .. *A61B 5/14532* (2013.01); *A61B 2560/0223* (2013.01); *A61B 2562/028* (2013.01); *A61B 2562/0285* (2013.01); *A61B 2562/04* (2013.01); *A61B 2562/125* (2013.01)

(56) References Cited

U.S. PATENT DOCUMENTS

| | | | |
|---|---|---|---|
| 2005/0272989 A1* | 12/2005 | Shah | A61B 5/14532 600/345 |
| 2006/0169481 A1 | 8/2006 | Stotz | |
| 2009/0198117 A1* | 8/2009 | Cooper | A61B 5/14532 600/347 |
| 2010/0025238 A1* | 2/2010 | Gottlieb | A61B 5/14532 204/401 |

OTHER PUBLICATIONS

Guiseppi-Elie, A.; Rahman, A. R. A.; Shukla, N. K., "SAM-modified microdisc electrode arrays (MDEAs) with functionalized carbon nanotubes" Electrochimica Acta 55 (2010) 4247-4255.

Johnson, K. W.; et al. "In vivo evaluation of an electroenzymatic glucose sensor implanted in subcutaneous tissue" Biosen. Bioelectron. 1992, 7, (10), 709-714.

Li, C.; Han, J.; Ahn, C. H., "Flexible biosensors on spirally rolled micro tube for cardiovascular in vivo monitoring" Biosen. Bioelectron. 2007, 22, (9-10), 1988-1993.

McMahon, C. P.; Killoran, S. J.; O'Neill, R. D., "Design variations of a polymer-enzyme composite biosensor for glucose: Enhanced analyte sensitivity without increased oxygen dependence" Journal of Electroanalytical Chemistry 580 (2005) 193-202.

Qiang, L. et al., "Highly sensitive and reusable Pt-black microfluidic electrodes for long-term electrochemical sensing" Biosensors and Bioelectronics; 26, 2; 682-688 (2010).

Wilson, G. S.; Gifford, R., "Biosensors for real-time in vivo measurements" Biosensors and Bioelectronics 20 (2005) 2388-2403.

* cited by examiner

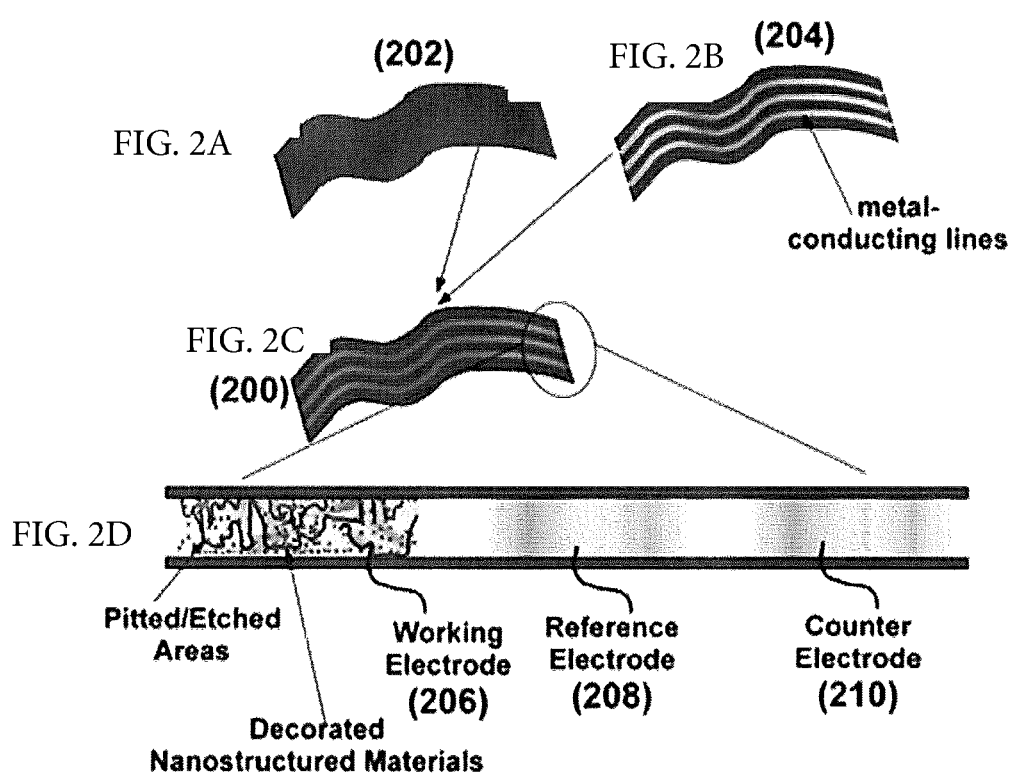

SENSORS FOR ANALYTE DETECTION AND METHODS OF MANUFACTURE THEREOF

CROSS-REFERENCE TO RELATED APPLICATIONS

This application claims is a divisional application of U.S. patent application having Ser. No. 13/164,656 filed on Jun. 20, 2011, which claims priority to U.S. Provisional Patent Application No. 61/398,498 filed on Jun. 25, 2010, the entire contents of which are hereby incorporated by reference.

STATEMENT OF GOVERNMENT SUPPORT

The present invention was developed in part with funding from the US Army/TATRC under Grant #W81XWH-07-10668 and Grant #W81XWH-09-1-0711. The United States Government has certain rights in this invention.

BACKGROUND

This disclosure relates to sensors for analyte detection and to methods of manufacture thereof. More specifically, this disclosure relates to biosensors and to methods of detection of biological metabolites and other analytes.

Numerous clinical trials and intensive research efforts have indicated that continuous metabolic monitoring holds great potential to provide an early indication of various body disorders and diseases. In view of this, the development of biosensors for the measurement of metabolites has become an area of significant scientific and technological study for various research groups across the world. A useful class of biosensors are electrochemical sensors that link enzymatic reactions to electroactive products. These sensors also enable the detection of small volumes of bio-analytes in clinical or home use applications. For example, the development of miniaturized implantable sensors for continuous monitoring of glucose is useful for optimal care of diabetes mellitus. Many other clinical situations also necessitate the measurement of various body metabolites like lactate, creatinine, creatine, glutamate, phosphate, cysteine, homocysteine, and the like. For example, a device that can measure lactate levels has important implications in a number of diseases and conditions (e.g., to indicate muscle fatigue, shock, sepsis, kidney disorders, liver disorders and congested heart failure). In some clinical situations, simultaneous monitoring of two or more metabolites is desirable.

For example, the complex interrelationship between glucose and other metabolic analytes induces one to simultaneously detect glucose, glutamate, lactate, oxygen, carbon dioxide, and the like. Simultaneous monitoring of brain glucose, lactate and oxygen gives a comprehensive picture of complementary energy supply to the brain in response to acute neuronal activation. Levels of glucose and glutamate in cerebrospinal fluid are important in the control of diseases such as meningitis.

Currently, most of the electrochemical sensors used for the specific detection of lactate, glucose, glutamate, and the like, employ analyte specific enzymes, and are based on the Clark-type amperometric detection. For example, first generation Clark-type glucose sensors employ the glucose oxidase enzyme ($GO_x$), immobilized on top of a working electrode. This enzyme catalyses the oxidation of glucose to glucarolactone, as shown in reaction (1).

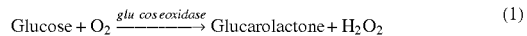

$$\text{Glucose} + O_2 \xrightarrow{\text{glu cos eoxidase}} \text{Glucarolactone} + H_2O_2 \quad (1)$$

The generated $H_2O_2$ is amperometrically assessed on the surface of a working electrode according to reaction (2) shown below.

$$H_2O_2 \xrightarrow{V} O_2 + 2H^+ + 2e^- \quad (2)$$

Currently, these biosensors suffer from two major pitfalls: (i) lack of miniaturization compatible with roll-to-roll production and (ii) lack of high sensor performance that is desirable for most of the in vivo applications.

The desire for miniaturization occurs from the complex applications these biosensors are being utilized for. Typical applications for these in vivo biosensors include metabolite monitoring in the neurons, extra cellular space, eyes, subcutaneous (s.c.) tissue, veins, and the like. In some cases, the biosensor is used in the affected area of the particular organ to diagnose the ailment and is left in place to monitor the condition of the ailment. In all of these applications, it is desirable to have miniaturization in order to avoid damage to the healthy tissue and to reduce wound recovery time, infection and patient discomfort.

Miniaturization of biosensors and sensor performance are two diametrically opposed issues. For example, most of the current miniaturization strategies result in a decrease in sensor performance as a result of reduced active working area, reduced enzyme loading and reduced signal-to-noise ratio. Any increase in the size of the biosensor will cause a large damage to the local tissue that will augment the magnitude of a foreign body response. This foreign body response will further decrease sensor performance by decreasing the analyte flux and possibly denaturing the sensing enzymes.

To alleviate some of the aforementioned issues of miniaturization, a number of micro-sensory devices based on microelectromechanical systems (MEMS) technology have been reported with advantages such as high precision, high functionality and mass-production. However, this technology uses expensive equipment and materials that could lead to an overall increase in the cost per piece of the biosensor. Moreover, these devices are based on inflexible or brittle materials such as silicon and glass, which have a higher chance of breakage within the in vivo environment.

In order to simultaneously afford miniaturization while at the same time increasing enzyme loading (to improve sensor performance), a silicon micro-machined needle-shaped structure for glucose monitoring has been reported. These needle-shaped biosensors along with channels for fluid flow and enzyme housing are created by wet and dry etching processes, while the (Ti/Pt) titanium/platinum working and (Ag/AgCl) silver/silver chloride reference electrodes located at the tip of the needle-shaped biosensors are patterned by photolithography. However as mentioned above, since these devices are made up of silicon substrates, these are more prone to breakage within the body.

In order to avoid the problem of sensor breakage in the body, biosensors have been fabricated, where the sensing electrodes are patterned on a polymeric KAPTON® film and subsequently rolled up to form a two dimensional cylindrical electrode. While the soft and flexible nature of these sensors presents an advantage over currently available techniques, these sensors are not reproducible on large scale and have a large sensor-to-sensor variability because of the large effect of the roll-up angle on the performance of the sensor. Moreover, the problem of enzyme loading and low electroactive surface still persists.

Biosensor miniaturization based on electrodes patterned on planar (both rigid as well as flexible) substrates have also been reported. However, these planar sensors do not afford 3-D analyte diffusion that is desirable for enhanced sensor performance. For enhanced sensor performance, miniaturized sensors based on micro-disc array electrodes have been reported, which use expensive machinery and cannot be easily produced at lower cost. Furthermore, these have problems of low electroactive area, lack of reusable electrodes and reduced enzyme loading.

Various reports have also emerged on the use of electrodes decorated with nanostructured materials such as nanoparticles, nanotubes and nanocubes to enhance the electroactive areas and enzyme loading. These nanostructured materials tend to be fouled very quick, thereby resulting in a quick loss of sensor performance.

Based on the above, it is desirable to develop methodologies for the production of biosensors that simultaneously afford extreme miniaturization, high sensor performance and flexibility for roll-to-roll production. Such methodologies will improve the quality of point of care diagnosis and prognosis of various body disorders.

SUMMARY

Disclosed herein is a sensor comprising a conduit; the conduit comprising an organic polymer; a working electrode; the working electrode being etched and decorated with a nanostructured material; a reference electrode; and a counter electrode; the working electrode, the reference electrode and the counter electrode being disposed in the conduit; the working electrode, the reference electrode and the counter electrode being separated from each other by an electrically insulating material; and wherein a cross-sectional area of the conduit that comprises a section of the working electrode, a section of the reference electrode and a section of the counter electrode is exposed to detect analytes; and wherein an old section of the sensor can be severed off to expose a new section of the sensor that can be used to detect analytes.

Disclosed herein too is a sensor comprising a first tape; a second tape; the second tape being opposedly disposed on the first tape and in contact with the first tape; a working electrode, a reference electrode and a counter electrode, each being disposed between the first tape and the second tape; the working electrode, the reference electrode and the counter electrode not being in contact with one another; and wherein a cross-sectional area of the sensor that comprises a section of the working electrode, a section of the reference electrode and a section of the counter electrode is exposed to detect analytes; and wherein an old section of the sensor can be severed off to expose a new section of the sensor.

Disclosed herein too is a method comprising disposing in a conduit, a working electrode; a reference electrode; and a counter electrode; the working electrode, the reference electrode and the counter electrode being separated from each other by an electrically insulating material; cutting the conduit to expose a section of the working electrode; a section of the reference electrode and a section of the counter electrode; etching the exposed section of the working electrode; and decorating the exposed section of the working electrode.

Disclosed herein too is a method comprising disposing a working electrode, a reference electrode and a counter electrode between a first tape and a second tape; wherein the working electrode, the reference electrode and the counter electrode are not in contact with one another; cutting the first tape and the second tape to expose a cross-sectional surface area of the working electrode, the reference electrode and the counter electrode; etching the exposed surface of the working electrode; and decorating the etched surface of the working electrode.

Disclosed herein too is a method comprising disposing a plurality of thin wires within a conduit; the thin wires being electrically separated by an insulating layer; cutting the conduit into a thin slice; polishing both sides of the conduit to expose a cross-sectional area of the thin wire; electrochemically etching the exposed cross-sectional area of the thin wire; coating the exposed cross-sectional area with electro-catalytic moieties suitable for the catalysis of a given redox species; connecting a cross-sectional are of the thin wire that is opposed to the etched cross-sectional area to an active matrix that is in turn connected to an appropriate microelectronic device for signal detection; where the active matrix switches and interrogates different thin wires.

Disclosed herein too is a sensor comprising a sensor housing; an active matrix addressing chip; a plurality of electrodes disposed within an electrically insulating casing; where each electrode has a cross-sectional area that is exposed to ambient surroundings; and wherein an opposing cross-sectional area of each of the electrodes contacts the active matrix addressing chip; and wherein the active matrix addressing chip and the plurality of electrodes being disposed in a sensor housing.

BRIEF DESCRIPTION OF THE FIGURES

FIG. 2A is a schematic representation of a biosensor configuration of a sensor, fabricated on a KAPTON® tape or similar flexible 'tape' like materials. It reflects a first tape which forms a first side of the sensor;

FIG. 2B is a schematic representation of a biosensor configuration of a sensor, fabricated on a KAPTON® tape or similar flexible 'tape' like materials. In this figure, at least three electrically conductive wires (e.g., in the form of lines) are disposed on the tape;

FIG. 2C is a schematic representation of a biosensor configuration of a sensor, fabricated on a KAPTON® tape or similar flexible 'tape' like materials. This figure is a depiction of the sensor that contains the first tape, the opposing second tape and the wires;

FIG. 2D is a cross-section of the sensor taken from the FIG. 2C. In the FIG. 2D, the working electrode, the reference electrode and the counter electrode are disposed side-by-side between the first tape and the second tape.

DETAILED DESCRIPTION

Figure 1A:
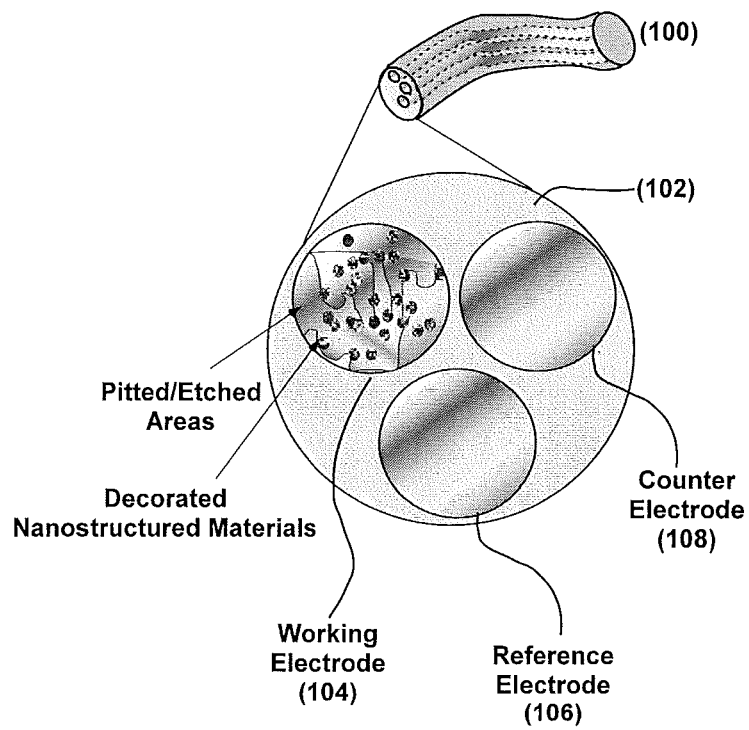
FIG. 1A is a schematic representation of a biosensor configuration when fabricated in a tubular structure.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The transition term "comprising" encompasses the transition terms "consisting of" and "consisting essentially of."

The term "flexible" as used herein is used to indicate that the device can be configured to take any desired position and can remain in this position for a desirable period of time. The device can return to its original position upon the application of a stimulus.

Various numerical ranges are disclosed herein. These ranges are inclusive of the endpoints as well as numerical values between these endpoints. The numbers in these ranges and those on the endpoints are interchangeable.

Disclosed herein is a flexible, miniature, reusable sensor that can be used for the detection of analytes and other biological metabolites. The sensor can be placed in-vivo and will have minimum invasive effect on the body of a living being. Disclosed herein too is a method of manufacturing the sensor. The sensor comprises a plurality of electrodes disposed in a flexible conduit. In an exemplary embodiment, the sensor comprises at least three electrodes—a first electrode or a working electrode, a second electrode or a counter electrode and a third electrode or a reference electrode disposed in the flexible conduit and contacted on their respective peripheries by the conduit. In a variation, the reference and the counter electrode could be the same electrode.

The sensor configuration utilizes the 'edge' or a "cross sectional area" or "cross sectional area surface" of an inert metal wire (such as platinum, gold, silver, palladium, and the like) as a working electrode. This metal wire is placed next to two other metal wires each of which will serve as a reference and a counter electrode respectively. The three metal wires are placed in an ultra thin, flexible tubing and fixed in place with a polymer conduit. One end of this conduit is cut along its short axis to expose the edges of the three metal wires, the surfaces of which will serve as the active areas of working, reference and counter electrodes. This configuration affords sensor regeneration, in that a new surface of these three electrodes can be readily obtained by cutting the tubing at a different place.

The method for manufacturing the sensor comprises disposing a conduit on the three electrodes. The conduit can be extruded onto the three electrodes or alternatively the three electrodes can be coated with a monomeric solution which is then cured to form the polymeric conduit. The sensor, which comprises the conduit with the three electrodes is then cut at an angle that is perpendicular to a longitudinal axis of the conduit. The working electrode is then etched and decorated with nanostructured materials. The etching and nanostructuring of the working electrode makes the working electrode highly sensitive, thereby improving the sensitivity and limit of detection of the sensor. The working electrode is also periodically cleaned in order to renew its activity.

In one method of using the sensor, the working electrode is coated with an enzyme or a plurality of enzymes, which will interact with an analyte of choice to produce an electroactive species. By changing the potential across the electrodes, the concentration of the electroactive species can be sensed and determined.

FIG. 1A is a schematic depiction of a cross-section of the sensor 100 that comprises a conduit 102 in which are disposed three wires which serve as the working electrode 104, the reference electrode 106 and the counter electrode 108 respectively.

The conduit may have a cross-sectional area that is circular, rectangular, square, triangular, polygonal, ellipsoidal, or a combination comprising at least one of the foregoing shapes. The cross-sectional area may be specially fabricated to conform to a particular cavity of space available in the body of a living being.

It is desirable for the conduit to be flexible so that it can be easily bent by hand. In one embodiment, the conduit has an elastic modulus less than or equal to about $10^6$ Pascals, specifically less than or equal to abut $10^5$ Pascals. In another embodiment, the sensor has an elastic modulus less than or equal to about $10^6$ Pascals, specifically less than or equal to abut $10^5$ Pascals.

The conduit generally comprises an organic polymer. Organic polymers include a wide variety of thermoplastic polymers, blend of thermoplastic polymers, thermosetting polymers, or blends of thermoplastic polymers with thermosetting polymers. The organic polymer may also be a blend of polymers, copolymers, terpolymers, or combinations comprising at least one of the foregoing organic polymers. The organic polymer can also be an oligomer, a homopolymer, a copolymer, a block copolymer, an alternating block copolymer, a random polymer, a random copolymer, a random block copolymer, a graft copolymer, a star block copolymer, a dendrimer, a polyelectrolyte (polymers that have some repeat groups that comprise electrolytes), a polyampholyte (a polyelectrolyte having both cationic and anionic repeat groups), an ionomer, or the like, or a combination comprising at last one of the foregoing organic polymers.

It is desirable for the organic polymer to be an elastomer at the body temperature of the living being into whom the sensor is inserted. In one embodiment, the organic polymer is a shape memory polymer that can return to a predetermined shape at the body temperature of the living being into whom the sensor is inserted.

Examples of the organic polymers are polyacetals, polyolefins, polyacrylics, polycarbonates, polystyrenes, polyesters, polyamides, polyamideimides, polyarylates, polyarylsulfones, polyacrylates, polymethacrylates, polyethersulfones, polyphenylene sulfides, polyvinyl chlorides, polysulfones, polyimides, polyetherimides, fluoropolymers, polyfluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, perfluoroelastomers, fluorinated ethylene propylene, perfluoroalkoxyethylene, polychlorotrifluoroethylene, polyvinylidene fluoride, polysiloxanes, or the like, or a combination comprising at least one of the foregoing organic polymers.

Examples of polyelectrolytes are polystyrene sulfonic acid, polyacrylic acid, pectin, carageenan, alginates, carboxymethylcellulose, polyvinylpyrrolidone, or the like, or a combination comprising at least one of the foregoing polyelectrolytes.

Examples of thermosetting polymers include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination comprising at least one of the foregoing thermosetting polymers.

Examples of blends of thermoplastic polymers include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleicanhydride/acrylonitrile-butadiene-styrene, polyether etherketone/polyethersulfone, polyether etherketone/polyetherimide polyethylene/nylon, polyethylene/polyacetal, or the like.

In one embodiment, biodegradable polymers can also be used to manufacture the conduit. Suitable examples of biodegradable polymers are as polylactic-glycolic acid (PLGA), poly-caprolactone (PCL), copolymers of polylactic-glycolic acid and poly-caprolactone (PCL-PLGA copolymer), polyhydroxy-butyrate-valerate (PHBV), polyorthoester (POE), polyethylene oxide-butylene terephthalate (PEO-PBTP), poly-D,L-lactic acid-p-dioxanone-polyethylene glycol block copolymer (PLA-DX-PEG), or the like, or combinations comprising at least one of the foregoing biodegradable polymers. The biodegradable polymers upon undergoing degradation can be consumed by the body without any undesirable side effects.

In one embodiment, an exemplary polymer is a thermosetting polymers. An example of a suitable elastomeric thermosetting polymer for use in the conduit is polydimethylsiloxane. In another embodiment, an exemplary polymer is a fluoropolymers. An example of a suitable thermoplastic polymer for use in the conduit is polytetrafluoroethylene. In yet another embodiment, an exemplary polymer is a biodegradable polymer. An example of a suitable biodegradable polymer for use in the conduit is polylactic-glycolic acid (PLGA).

The conduit has a diameter effective to embed and to surround the three electrodes with sufficient space between them to prevent any electrical interference that may distort a signal. In one embodiment, the conduit is in intimate contact with the circumferential periphery of each of the electrodes.

As detailed above, the working electrode, the reference electrode and the counter electrode are each embedded in the conduit. The working electrode, the reference electrode and the working electrode each comprises an electrically conducting material such as for example a metal, a ceramic or a conductive polymer. Other electrically conducting materials can also be used to form each of the electrodes.

An exemplary electrically conducting material is a metal. Exemplary metals are platinum group metals or noble metals. Examples of suitable metals are platinum, gold, silver, palladium, rhodium, ruthenium, iridium, or the like, or a combination comprising at least one of the foregoing metals.

Examples of suitable electrically conducting ceramics are indium tin oxide, indium zinc oxide, antimony oxide, zinc oxide, or the like, or a combination comprising at least one of the foregoing ceramics.

Examples of suitable electrically conducting polymers are polyaniline, polypyrrole, polyacetylene, polythiophene, or the like, or a combination comprising at least one of the foregoing electrically conducting polymers.

Examples of other conducting materials that can be used as the working electrode, the reference electrode or the counter electrode are carbon fibers, carbon nanotubes (e.g., single wall carbon nanotubes, double carbon wall nanotubes, multiwall carbon nanotubes), metal coated fibers, or the like, or a combination comprising at least one of the foregoing fibers. Exemplary wires comprise gold, platinum or carbon fibers.

In one embodiment, each of the electrodes is manufactured from a biodegradable electrically conducting material. An example of a biodegradable electrically conducting material is one of the foregoing biodegradable polymers blended with an electrically conducting material such as carbon black, carbon nanotubes, intrinsically electrically conducting polymers (e.g., polypyrrole, polythiophene, polyaniline, polyacetylene, and the like).

The working electrode, the reference electrode and the counter electrode can each be in the form of a wire. The wire can be a single wire or can comprise multiple strands. In one embodiment, when multiple strands are used, the multiple strands are braided to form the wire, which serves as an electrode.

In one embodiment, the wire may be in the form of a ribbon. The wire has a circular cross-section while the ribbon has a rectangular cross-section. The wire generally has a diameter of about 5 nanometers to about 1000 micrometers, specifically about 100 nanometers to about 500 micrometers, and more specifically about 200 nanometers to about 25 micrometers. If the wire is in the form of a ribbon, the ribbon will have a width of a diameter of about 5 nanometers to about 100 micrometers, specifically about 10 nanometers to about 50 micrometers, and more specifically about 20 nanometers to about 25 micrometers.

The disposing of the conduit on the electrodes can be accomplished by extrusion. Cross-head extrusion is generally used to dispose the conduit on the electrodes. The extrusion process is generally conducted with thermoplastic or thermosetting polymers. In an exemplary embodiment, thermoplastic polymers are used in the extrusion process to manufacture the conduit.

In another embodiment, the conduit is disposed on the electrodes by molding. Thermoplastic polymers and/or thermosetting polymers may be used to manufacture the conduit in a molding process.

Alternatively, the electrodes may be coated with a common coating of a monomeric material. The monomeric material is then crosslinked to form a polymer. Crosslinking can be accomplished by ultraviolet (UV) curing, thermally induced crosslinking, infrared induced crosslinking, X-ray induced crosslinking, electron beam induced crosslinking, or a combination thereof. Thermosetting polymers result from the crosslinking of the monomers. Examples of thermosetting polymers are provided above.

In one embodiment, in a variation of the aforementioned configuration, the metal wires and the flexible conduit are replaced by three electrodeposited metal conducting lines, sandwiched between two pieces of a KAPTON® (polyimide) tape, Scotch Tape or any other ultra-thin flexible polymer with an adhesive backing. In this configuration, the surfaces of the three working electrodes are realized by cutting the 'tape sandwich' across the shorter edge (at an angle between 10 and 170 degrees and preferably between 45 and 90 degrees with respect to a perpendicular to the longer edge of the tape). The working electrode is further processed according to the aforementioned procedures detailed below to enhance its electro-active area and thereby its performance.

FIGS. 2A-2C are a depiction of the elements and the method used in the manufacturing of such a sensor. The FIG. 2A reflects a first tape which forms a first side of the sensor. In the FIG. 2B, at least three electrically conductive wires (e.g., in the form of lines) are disposed on the tape. The wires may be disposed on the tape by electrochemical deposition or by chemical vapor deposition using a mask to prevent metal deposition on those areas of the tape where deposition is not desired.

Electrochemical deposition involves exposing the tape to a metal containing solution and application of a constant potential or current. The application of constant potential or current includes techniques such as galvanometry, amperometry, potentiometry, cyclic voltammetry and the like. If combinations of the foregoing electrochemical deposition techniques are used, they may be employed simultaneously or sequentially.

Chemical vapor deposition includes atmospheric chemical vapor deposition, low pressure chemical vapor deposition, ultrahigh vacuum chemical vapor deposition, aerosol assisted vapor deposition, direct liquid injection chemical vapor deposition, microwave plasma assisted chemical vapor deposition, remove plasma enhanced chemical vapor deposition, atomic layer chemical vapor deposition, hot wire (hot filament) chemical vapor deposition, metal organic chemical vapor deposition, combustion chemical vapor deposition, vapor phase epitaxy, rapid thermal chemical vapor deposition, hybrid physical chemical vapor deposition, or a combination comprising at least one of the foregoing processes. If combinations of the foregoing chemical vapor deposition processes are used, they may be employed simultaneously or sequentially.

In case of use of electrochemical deposition for the disposition of the wires on the first tape, a thin layer of another organic film can be immediately deposited (using chemical vapor deposition) around the edges of the wires in order to increase their adhesion to the tape. Some examples of this organic thin film include hexamethyldisilazane, hexamethyldisiloxane, trichloromethylchlorosilanes, hexachloro disiloxane, tetramethyl(dichloromethyl)disiloxane and the like. Other materials such as the thermosetting or thermoplastic polymers (listed above) may also be used to form the thin layer of organic film.

Following deposition of wires, a second tape may be disposed on the wires. The second tape is opposedly disposed to the first tape. The second tape forms a second side of the sensor. The FIG. 2C is a depiction of the sensor that contains the first tape, the opposing second tape and the wires. Following the disposing of the second tape, the surface of one of the wires is etched and decorated with a nanostructured material to form the working electrode. The etching and the decorating of the working electrode are described in detail below. The disposing of the second tape, the etching and decorating and the cutting to expose an edge can be conducted in any desirable sequence. For example, the electrodes may be cut and decorated prior to disposing the second tape on the first tape and on the wires.

FIG. 2D is a cross-section of the sensor 200 taken from the FIG. 2C. In the FIG. 2D, the working electrode 206, the reference electrode 208 and the counter electrode 210 are disposed side-by-side between the first tape 202 and the second tape 204. In one embodiment, the first tape and the second tape contact each other via an adhesive. In another embodiment, the first tape and the second tape contact each other via an enzyme layer.

While the FIG. 2D depicts the working electrode, the reference electrode and the counter electrode arranged in order from left to right, the positions can be interchanged depending upon convenience. In addition, there can be more than three electrodes disposed upon the tape.

Following the disposing of the conduit on the electrodes, the conduit along with the wires is cut at an angle that is not perpendicular to the longitudinal axis of the conduit. The longitudinal axis of the conduit is one which is parallel to the circumferential surface of the conduit (i.e., it is concentric with the curved surface of the conduit). The cutting of the conduit generates an edge in the working electrode that can be used for detection, thus producing an edge-based sensor. The following procedures are then performed on the conduit to improve the performance of the sensor.

In one embodiment, the working electrode is selectively etched and decorated with nanostructured particles to enhance the sensitivity of the sensor.

Figure 1B:
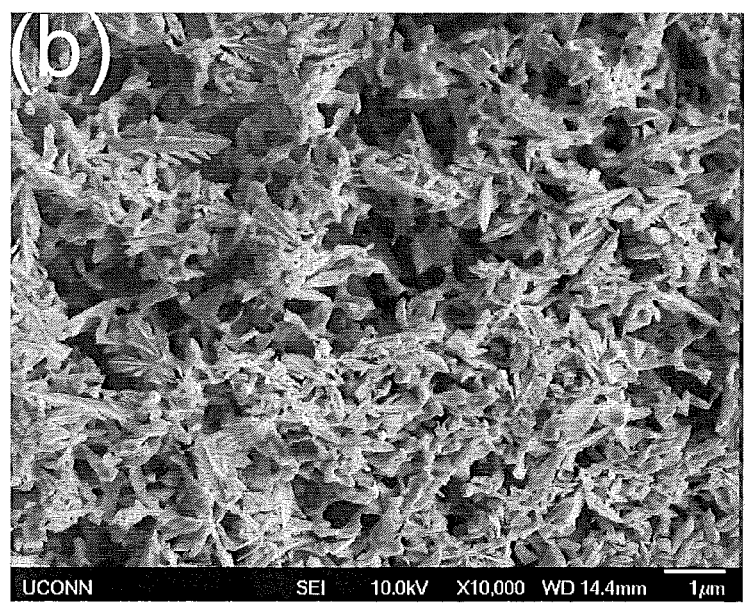
FIG. 1B is a scanning electron micrograph image of the etched Au wire edge.

The surface of the working electrode is selectively etched to enhance the electroactive area and is further decorated with highly activated nanostructured materials to enhance its activity towards electrochemical oxidation or reduction. FIG. 1B is a scanning electron micrograph image of an etched gold wire cross sectional surface.

Suitable etching agents can be either acidic or basic. Etching can be conducted simultaneously with an acid and then with a base or vice versa.

Examples of suitable acids for etching are hydrochloric acid, nitric acid, sulfuric acid, or the like, or a combination comprising at least one of the foregoing acids. Examples of suitable bases for etching the wires are potassium hydroxide, sodium hydroxide, ammonium hydroxide, sodium hydrogen phosphate ($Na_2HPO_4$) or the like, or a combination comprising at least one of the foregoing bases. Neutral solutions can also be used for etching. Exemplary solutions are basic (alkaline) solutions.

In one embodiment, directed to the pitting and etching process, a potential is applied between the working and the reference electrode to accelerate the pitting and etching process.

Figure 1C:
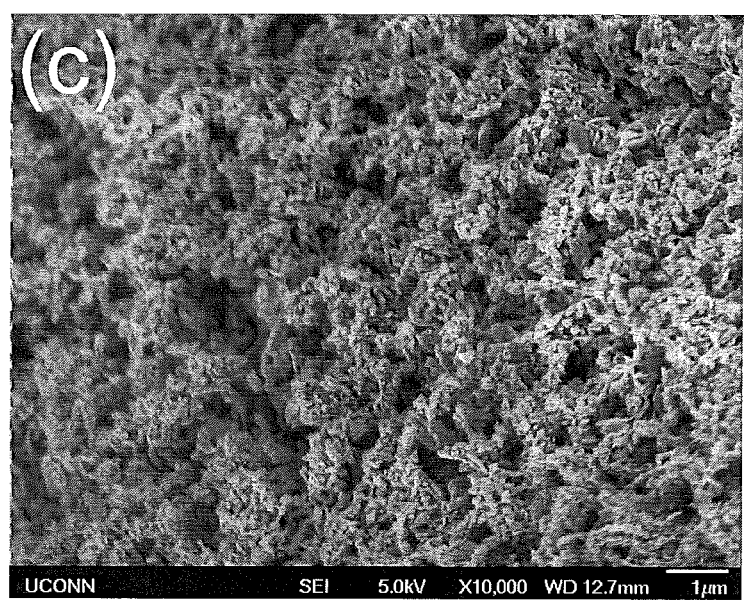
FIG. 1C is a scanning electron image of the etched Au wire edge and subsequently Platinum-decorated etched Au wire edge.

In yet another embodiment, the 'pitted and/or etched' working electrode is decorated with nanostructured materials by exposing the working electrode to a solution of the nanostructured materials and by applying a constant potential or current and preferably potential between the working and the reference electrodes. The nanostructured material could be a nanoparticle, nanotube or a nanocube. These nanostructured materials can comprise platinum, silver, iridium, rhodium, gold, palladium, carbon, graphene, diamond, or the like, or a combination thereof. In an exemplary embodiment, the nanostructured material is carbon or platinum. FIG. 1C is a scanning electron image of the etched gold wire (electrode) edge that is subsequently decorated with platinum. The term or prefix "nano" encompasses structures that have average particle sizes of less than or equal to about 200 nanometers, specifically less than or equal to about 100 nanometers.

In a variation of the aforementioned process, the nanostructured material can be co-deposited with a polymeric membrane by exposing the working electrode to a solution contacting both the nanostructured materials and a monomer and by applying a constant potential or current and preferably potential between the working and the reference electrode. The concentration of the monomer can be varied and the monomer can be can be selected from the group consisting of ortho-phenylene diamine (OPD), para-phenylene diamine, meta-phenylene diamine, phenol, pyrrole, flavins, naphthalene, aniline, thiophenes, sulfonated aniline, sulfonated pyrrole, or the like, or a combination thereof.

In a variation of the aforementioned process, the nanostructured material is coated with the monomer and then co-deposited on the surface of the working electrode, by applying a potential or a current between the working and the reference electrode.

In another embodiment, the working electrode is coated with a specific set of enzymes, at least one of which will initiate a reaction with an analyte of interest to produce an electroactive species. The enzymes selected from the group consisting of transferases, hydrolases, oxidases, peroxidases, kinases, superoxidases, phosphatases, or the like. Enzyme deposition can be achieved by methods such as drop casting, dip coating, spin coating, spray coating and electrodeposition. In an exemplary embodiment, the enzyme deposition can be accomplished via electrodeposition. This electrodeposition can be achieved by applying a constant current or a potential across the working and the reference electrodes. In an exemplary embodiment, the electrodepositon is achieved by applying a constant potential across the working and the reference electrodes.

In a variation of the aforementioned process, the enzyme can be co-deposited with a polymeric membrane by exposing the working electrode to a solution containing both the enzyme and a monomer and by applying a constant potential or current between the working and the reference electrode. A constant potential is preferred for this enzyme deposition. The concentration of the monomer can be varied and the monomer can be selected from the group consisting of ortho-phenylene diamine (OPD), para-phenylene diamine, meta-phenylene diamine, pyrrole, flavins, naphthalene, aniline, phenols, thiophenes, sulfonated aniline, sulfonated pyrrole, and the like. In an exemplary embodiment, the monomer is OPD.

In a variation, the enzyme is first deposited on the wire that forms the working electrode before disposing it in the conduit.

In one embodiment, the enhanced activity of the decorated nanostructured material is preserved by periodic cleaning of the working electrode in a buffer solution, by any one of processes selected from electrochemical cleaning, etching, sonication, or combinations thereof. Electrochemical cleaning is preferred.

In a variation of the aforementioned methodology, the cleaning is performed in a buffer solution whose pH is acidic, neutral or alkaline. In an exemplary embodiment, the cleaning is performed in an acidic buffer solution. In a variation of the aforementioned methodology, the cleaning is performed in a quiescent, stirred or flowing buffer solution and preferably in a flowing buffer solution.

In another embodiment, the cleaning is performed in a non-quiescent environment by desorbing the poisoning species and adsorbing/polymerizing them onto a nearby electrically conductive structure. Such a structure can be an overlayer on top of the pitted/etched and nanomaterial-decorated working electrode edge. This overlayer can comprise a polymeric film made up of but not limited to polyvinylchloride, polycarbonate, polyvinylacetate, humic acids, cellulose acetate, polythiophenes, polyphenylene diamines, polypyrroles, polynaphthalenes, polyphenols, or the like, or a combination thereof. In addition, this over layer can be deposited via spin coating, drop casting, dip coating, layer-by-layer assembly, inkjet printing, spray coating and electropolymerization. In an exemplary embodiment, the overlayer is deposited via electropolymerization.

The sensor works on the principle of electrochemical oxidation or reduction of the electroactive species that is either present in the in vivo environment or produced as a result of reaction between the enzyme and the analyte to be detected. The electrochemical oxidation or reduction is achieved by applying a potential between the working electrode wire and reference electrode wire. This electrochemical oxidation or reduction produces a current at the working electrode that can be measured using an electronic unit.

This sensor is advantageous in that it is suitable for the simultaneous detection of more than one analyte. This can be readily accomplished by increasing the number of wires in the conduit or the number of metal conducting lines in the tape based 'edge' biosensors. The tape comprises a material selected from the group consisting of paper, polyester, polyimide, polyetherimide, polyolefin, polytetrafluoroethylene, polysiloxane, or a combination of at least one of the foregoing materials.

In the event that additional wires are disposed in the conduit, each wire is coated with an enzyme specific to the analyte of interest. All other processes such as pitting/etching, decoration with nanostructured materials and cleaning remain the same.

Figure 10:
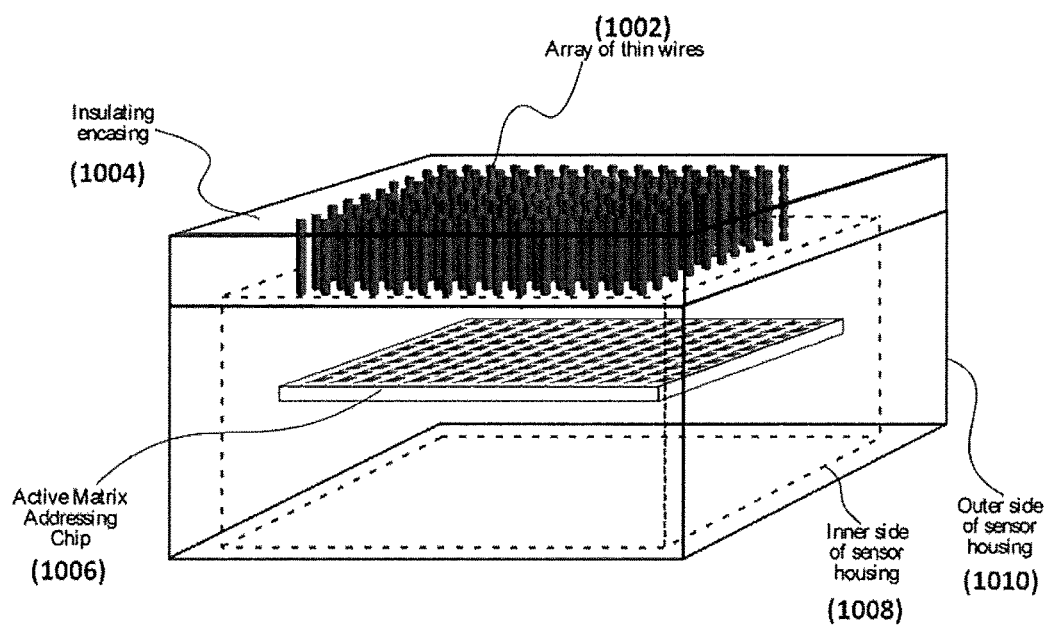
FIG. 10 is a schematic configuration of interfacing a multi-wire sensor geometry to an active matrix addressable chip located within a protective encasing. This will allow addressing individual wire edge plane sensors with minimum interconnects.

In the event that additional wires are disposed in the conduit, each wire can be independently addressed via an active matrix element. The FIG. 10 is a depiction of an exemplary sensor that comprises a plurality of wires (electrodes) that are greater in number than the 3 electrodes of the FIGS. 1A and 2D. With respect to the FIG. 10, the sensor comprises an array of wires (electrodes) 1002 disposed in an electrically insulating casing 1004. The insulating casing 1004 comprises an internal cavity termed the sensor housing 1008. The sensor housing has an external surface 1010 that forms the outside of the sensor housing 1010. The electrodes 1002 are disposed on an active matrix addressing chip 1006. The active matrix addressing chip 1006 along with the electrodes are disposed in the cavity on the inner side of the sensor housing 1008. A cross-sectional surface area of the electrodes are exposed to contact analytes for purpose of detection and analysis.

In one embodiment, a method for manufacturing the sensor of the FIG. 10 comprises disposing an array of thin wires (electrodes) disposed within a conduit where the thin wires are electrically separated by an insulating layer. The conduit is then cut to expose edges (cross sectional area) of the electrodes. The exposed edges are electrochemically etched to increase their surface area. The electrochemically etched surface is coated with nano-sized electro-catalytic moieties suitable for the catalysis of a given redox species, where the electrocatalytic moieties are surface coated with a thin polymeric film that is semi permeable to small molecules but impermeable to large molecular interferences. The nano-sized electro-catalytic moieties can be regenerated by applying a cyclic potential in an aqueous solution. The nano-sized electro-catalytic moieties when contacted by the metabolite can produce an electrical signal that is detected with the appropriate microelectronics.

The opposing cross sectional surface area of the electrodes is in electrical communication with an active matrix that in turn communicates with appropriate microelectronics for signal detection. The active matrix is capable of switching and interrogating between different electrodes.

In order to expose a cross-sectional surface of the electrodes, after the wires are disposed in the conduit, both sides of the conduit are cut perpendicular to the long axis of the conduit to expose the wire edges. On one side, all processes such as pitting/etching, decoration with nanostructured materials and cleaning are performed. The other side of the edges are connected to an active matrix (via flip-chip bonding, ultra sonic bonding, electropolymerization, conductive adhesives, soldering micro- or nanobeads, and the like) that is in turn connected to the appropriate microelectronics for signal detection. The active matrix is capable of switching and interrogating between different said thin wires and minimizes the number of interconnects within the device encasing.

This sensor is advantageous in that it allows for the elimination of non specific adsorption of one enzyme on another working electrode during the fabrication of the aforementioned multi-analyte sensors. This is achieved by masking the concerned working electrodes via dipping the electrode in electroplating solutions (such as Cu, Cr, Ag, Zn, and the like), thiol or allyl derivatives solution, which can be removed subsequently by applying a fixed potential.

Another advantage of this sensor is its ability to perform an internal calibration routine to account for foreign body response and biofouling, which are known to degrade enzyme activity and analyte flux. This can be achieved by utilizing two working electrodes, wherein both the surfaces are pitted/etched and decorated with the nanostructured materials, but only one is coated with an enzyme. This enzyme is selected in such a way that it specifically reacts with the analyte of interest to produce a product which is electroactive at the surface of the working electrode. The internal calibration of the enzyme coated working electrode can be achieved by comparing its background currents with that of the background currents of the blank working electrode and through the differential offsetting of the background currents of the enzymatic working electrodes with respect to the blank working electrode. Since the background current is independent of enzymatic activity and analyte flux, the procedure will allow for an estimation of the magnitude of the foreign body response and therefore will facilitate internal self calibration.

In yet another advantage, the sensor is suitable to achieve three-dimensional diffusion of the analyte towards the working electrode. Three-dimensional diffusion of analyte towards the working electrode is preferred in order to improve sensor sensitivity and limit of detection. The sensor of FIG. 1A (100) or FIG. 2 (200) by itself affords three dimensional diffusion, but it can be further enhanced by increasing the number of wires in the conduit or the number of metal conducting lines in the tape based 'edge' biosensors. All other processes such as pitting/etching, decoration with nanostructured materials and cleaning remain the same.

The invention will be illustrated in more detail with reference to the following examples, but it should be understood that the present invention is not deemed to be limited thereto.

EXAMPLES

Example 1

Figure 3:
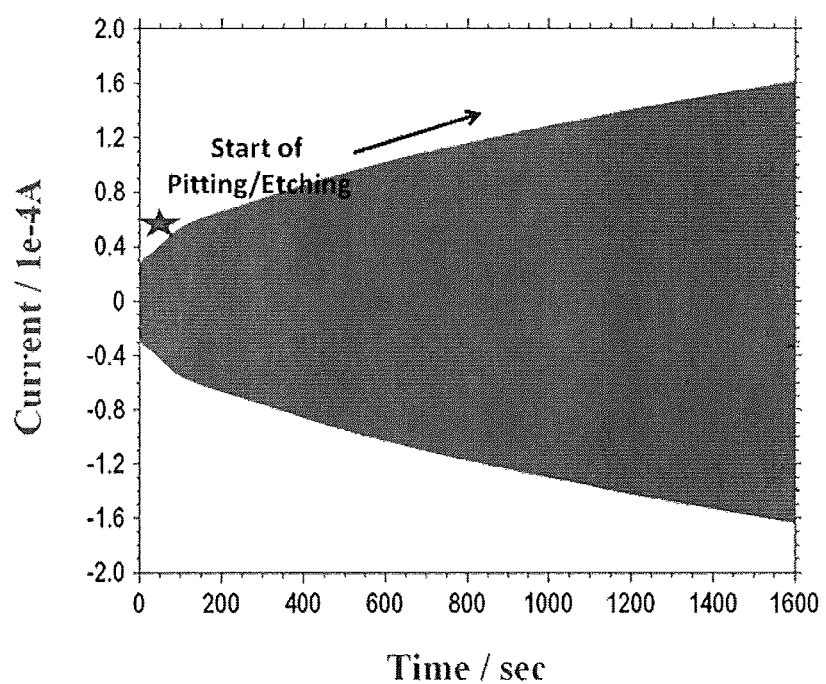
FIG. 3 is a response current as function of etching time during the pitting/etching process. Here, the bias is switched between +0.8 V and −1 V, with progressive increase in the response current due to the gradual increase in the surface area of the working electrode.

This example was conducted to demonstrate a method for pitting/etching on the surface of the working electrode to enhance its electrochemical area. The pitting/etching of the surface of the working electrode is achieved by exposing the working electrode to a stirred solution of 2 M NaOH (sodium hydroxide) solution and by applying a sequential potential of +0.8 V (volt) and −1 V for more than 15 minutes. As can be seen in FIG. 3, the response current increases with increasing time which is an indication of the pitting/etching process that also results in an increased surface area of the of the working electrode (see FIG. 1B).

Example 2

This example was conducted to demonstrate a method of increasing the electrochemical activity of the working electrode by sequential processes involving the pitting/etching of the surface of the working electrode followed by decoration with nanostructured materials.

At first the sensor of FIG. 1A is exposed to a stirred solution of 2M NaOH, while applying a sequential potential of +0.4 V and −0.8 V for about 15 minutes. Subsequently, this surface is decorated with platinum nanoparticles, by exposing the surface to 10 mM $H_2PtCl_6$ (chloroplatinic acid hexahydrate) in 0.1 M HCl and simultaneously applying a constant current of 12 microamperes/square millimeter for 15 minutes.

Figure 4:
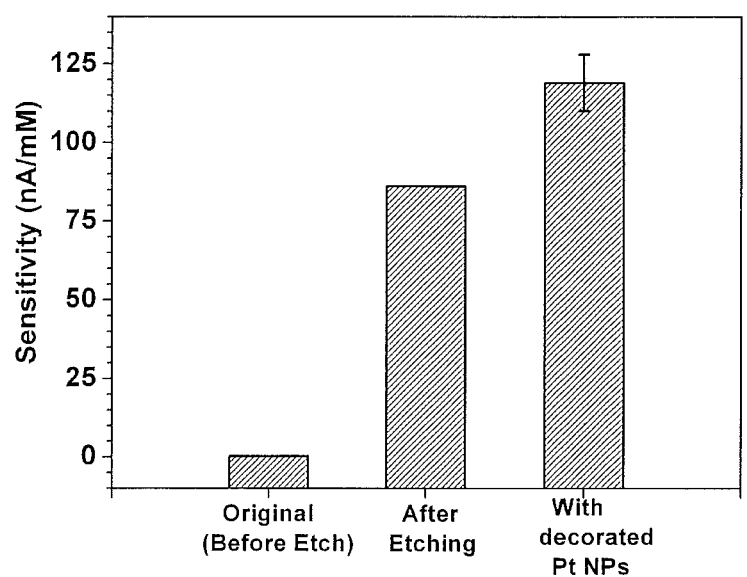
FIG. 4 depicts the sensitivity to $H_2O_2$ of a 25 micron wire-edge biosensor of FIG. 1A at its various stages of fabrication.

FIG. 4 illustrates the sensitivity of the sensor to $H_2O_2$ when tested at 0.6 V with respect to Ag/AgCl reference. As can be seen in FIG. 4, the pitting/etching of the surface of the working electrode enhances the (hydrogen peroxide) $H_2O_2$ sensitivity by 2 orders of magnitude, owing to the increased electrochemical active area (FIG. 1B). This $H_2O_2$ sensitivity is further enhanced by an additional 25% by decorating the pitted/etched surface of the working electrode with a thin layer of platinum nanoparticles. (FIG. 1C)

Example 3

This example illustrates a methodology to improve sensor sensitivity by a simple electrochemical cleaning process. The biosensor of FIG. 1A is decorated with platinum nanoparticles, as described in Example 2 and its sensitivity towards $H_2O_2$ before and after electrochemical cleaning is investigated. The electrochemical cleaning step involves subjecting the working electrodes to cyclic voltammetric sweeps (21 cycles in range −0.5 to +0.9 V at a rate of 100 millivolts/sec) in flowing phosphate buffer saline (PBS, pH=7.4) (30 microliters/minute).

Figure 5:
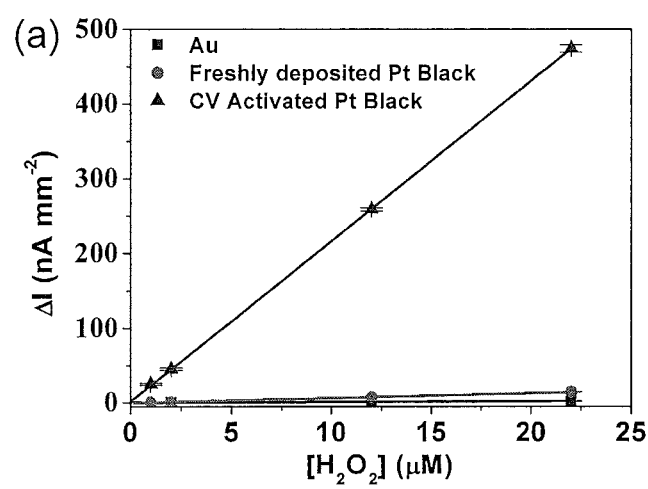
FIG. 5 depicts the sensitivity of the biosensor configuration to $H_2O_2$ before and after subjecting to an electrochemical cleaning procedure.

FIG. 5 shows the amperometric current versus $H_2O_2$ concentration for the "as fabricated" biosensor when operated at 0.4 V versus Ag/AgCl. The slopes of these curves represent the sensitivity for $H_2O_2$ detection. The sensitivity of the freshly deposited Platinum-black electrodes increased from 0.092 $nA \cdot \mu M^{-1}$ $mm^{-2}$ of the bare gold electrode to 0.65 $nA \cdot \mu M^{-1}$ $mm^{-2}$. Following electrochemical cleaning, the sensitivity of the sensor towards $H_2O_2$ increased by 33 times versus that of freshly deposited platinum electrodes, to a value of 22 $nA \cdot \mu M^{-1}$ $mm^{-2}$. This value is 240-fold larger than that for the Au electrodes alone. This improvement may be due to flow-induced removal of various adsorbed residues on the platinum black surfaces, along with the selective oxidation of platinum atoms that promote the formation of selected crystallographic planes.

Example 4

Figure 6:
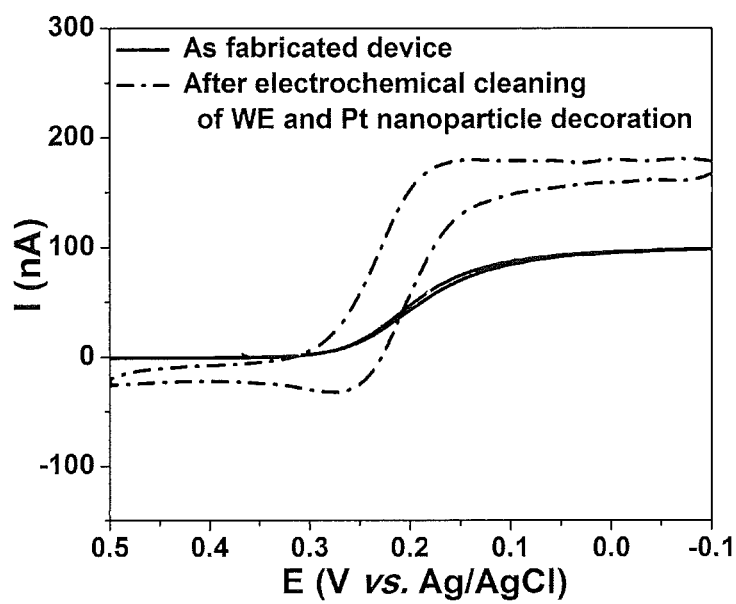
FIG. 6 is a graph showing a cyclic voltammogram in 10 mM $K_3(FeCN_6)$ in 1M KCl aqueous solution at 10 mV/s scanning rate of the biosensor configuration of FIG. 1A at various stages of it fabrication. The sigmoidal shapes of these curves indicate microelectrode behavior which in turn demonstrates 3-D analyte diffusion.

This example demonstrates the microelectrode behavior of edge plane sensors of the present disclosure. For this, the sensor of FIG. 1A (before and after subjecting to electrochemical etching and subsequent deposition of platinum nanoparticles) was subjected to cyclic voltammetry (CV) in 10 mM $K_3(FeCN_6)$ in 1M KCl aqueous solution at 10 mV/s scanning rate and the corresponding CV curves are shown in FIG. 6. The CV curves of these sensors exhibited a sigmoidal shape which is typical of microelectrode behavior. Moreover, the sigmoidal shape was retained even after electrochemical etching and platinum nanoparticle decoration of the working electrode.

Example 5

Figure 7A:
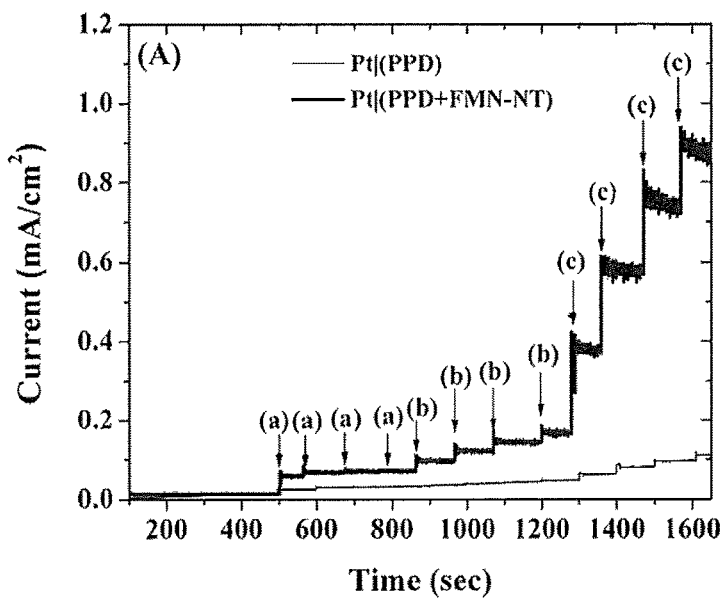
FIG. 7A is a graph showing amperometric response of working electrodes when coated with PPD and PPD+FMN-NT operated at 0.7 V versus Ag/AgCl reference for sequential additions of (a) 2 µM (b) 20 µM (c) 200 µM (d) 2000 µM of $H_2O_2$ as represented by downward arrows.

This example, illustrates a methodology wherein the biosensor of FIG. 1A can be decorated with a nanostructured material to enhance sensitivity, via by co-depositing the nanostructured material with a polymeric membrane. Apart from the enhancement in the sensor sensitivity, this methodology affords a significant advantage of sensor selectivity against electro-active endogenous species such as ascorbic acid, uric acid, acetaminophen, and the like. The latter is typically achieved via the use of ultra-thin electropolymerized films that act as permselective membranes that inadvertently reduces sensor sensitivity towards $H_2O_2$. The biosensor of FIG. 1 is coated with a thin layer of electropolymerized film of poly (phenylene diamine) (PPD) in the presence and absence of nanostructured materials based on flavin-wrapped single walled carbon nanotubes (FMN-NT). FIG. 7A shows the amperometric response of PPD and PPD+FMN-NT coated working electrodes to sequential additions of $H_2O_2$ operated at 0.7 V versus Ag/AgCl reference. As can be seen, both the sensors displayed an increase in their response upon addition of $H_2O_2$. However, for all $H_2O_2$ additions, the PPD+FMN-NT acted sensors showed a higher response compared to PPD coated sensors.

Figure 7B:
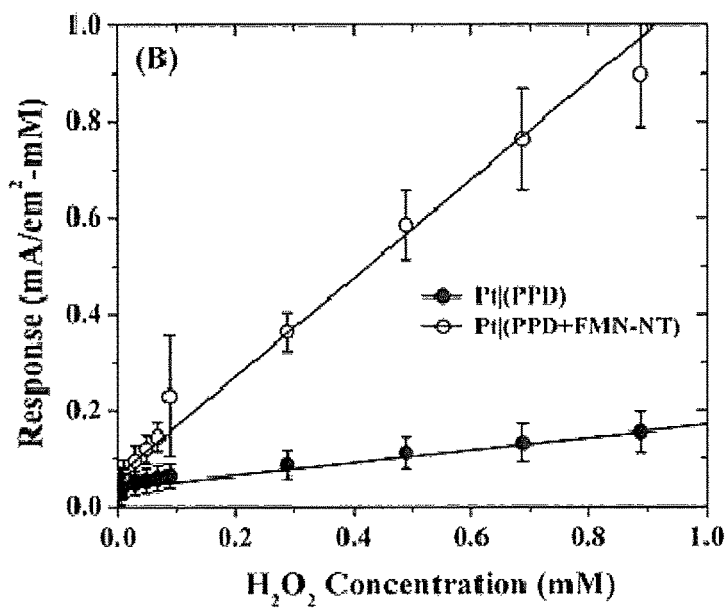
FIG. 7B is a graph showing saturation amperometric current versus $H_2O_2$ concentration for PPD and PPD+FMN-NT coated working electrode.

FIG. 7B illustrates the response of the PPD and PPD+FMN-NT coated sensor as a function of $H_2O_2$ glucose concentration. For both the sensors, the addition of $H_2O_2$ resulted in a linear increase in their amperometric response within the range of $H_2O_2$ tested. The PPD+FMN-NT sensors, however displayed a 5-6 fold higher response compared to PPD sensors, owing the enhanced electroactivity of the FMN-NTs.

Example 6

Figure 8:
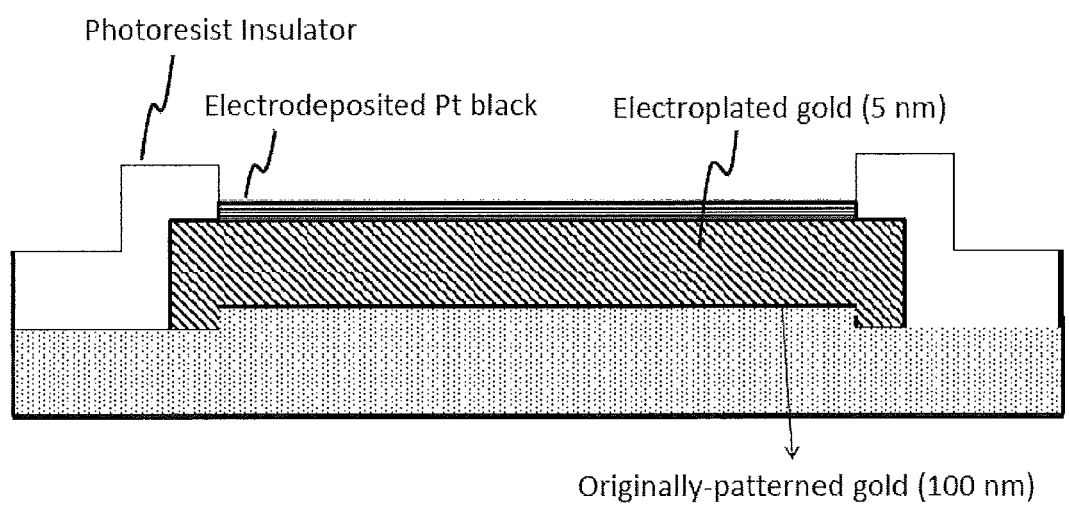
FIG. 8 depicts the configuration for obtaining a stable sensor structure in a planar configuration.

This example illustrates a methodology to obtain stable micro-electrodes. The stable microelectrodes are obtained on pre-cleaned glass slides. These substrates were then spin coated with 1.2 mm of photoresist film followed by baking (120° C., 10 min.) Following UV exposure, development and plasma cleaning, a 10 nm (nanometer) chromium/100 nm gold layer was evaporated and lifted off (in acetone) to afford electrode patterning. Subsequently, following an 8 hour vacuum treatment in hexamethyldisilazane (HMDS) vapors, a 2 μm thick positive photoresist was deposited and patterned to create coarse openings over all electrodes and contact pads. 1 hour of exposure in a gold plating solution (10 μA·mm$^{-2}$ current density) enabled the electroplating of 5 μm thick Au over the exposed gold electrodes. Subsequently, the entire device was rinsed in acetone to remove all photoresist, and re-spun coated with 2 μm of a final positive photoresist to define the final electroactive area of electrodes (with a circular opening of 900 μm in diameter) and 2×5 mm rectangular windows for contact pads. Working electrodes were realized by electrodepositing 300 nm of platinum in 10 mM H$_2$PtCl$_6$ and 0.1 M HCl at 12 μA·mm$^{-2}$ for 15 minutes. The final structure of working electrode is shown in FIG. 8.

Example 7

This example illustrates a methodology to modify a particular working electrode (without affecting the other working electrodes) of a microelectrode array containing a plurality of more than 3 working electrodes. This methodology is illustrated with a sensor similar to the one shown in FIG. 1A containing three working electrodes, one reference and one counter electrode. The sensor to be fabricated will be utilized as a multi-analyte device for simultaneous detection of glucose, lactate and oxygen. The detection of glucose and lactate is achieved by measuring the amperometric current produced by electrochemical oxidation of H$_2$O$_2$, produced as result of enzymatic reaction of glucose and lactate with glucose oxidase and lactate oxidase, respectively. Oxygen detection is achieved by measuring the amperometric current produced by its electrochemical reduction.

Figure 9A:
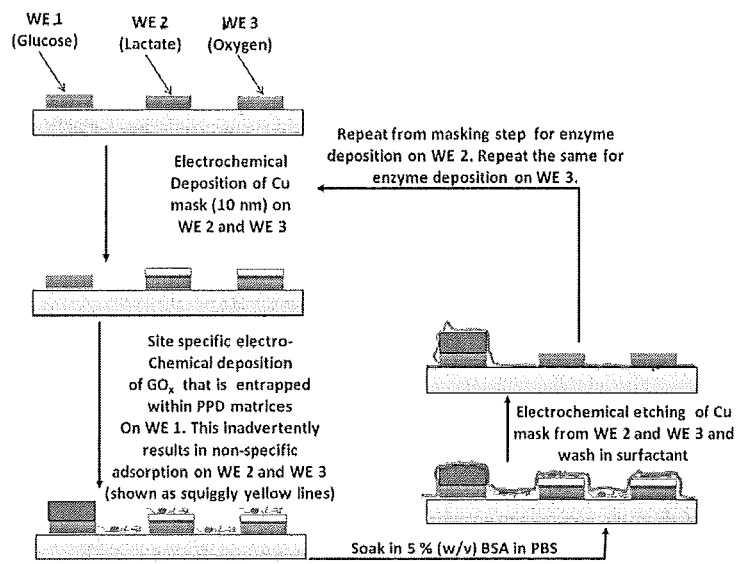
FIG. 9A is a schematic representation of various steps involved in masking methodology that is used to fabricate a multi-analyte sensor.
Figure 9B:
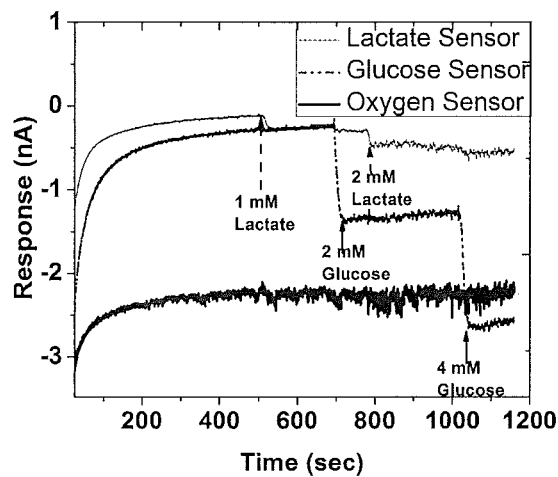
FIG. 9B shows the response of the multi-analyte (glucose, lactate and oxygen) sensor to changes in lactate and glucose concentrations.

The methodology to immobilize the specific enzyme on the specific working electrode involves a masking technique based on electrochemical deposition of copper and its subsequent removal via electrochemistry in neutral, aqueous solutions. A detailed schematic of this technique is shown in FIG. 9A. FIG. 9B shows the in vitro operation of the as fabricated multi-analyte sensor in a stirred PBS buffer solutions. The sensor was operated by biasing the glucose and lactate working electrode at 0.7 versus Ag/AgCl reference and the oxygen working element at −0.1 V versus Ag/AgCl reference. As seen in FIG. 9B, the addition of glucose to the test cell resulted in an increase in the response of only the glucose working element. Similarly, the addition of lactate to the test cell resulted in an increase in the response of only the lactate working element. Here it is worth noting that the response of the oxygen sensing element remained constant throughout the course of the experiment. These facts are indicative of the zero chemical crosstalk among these sensors which in turn indicate that the masking technology demonstrated in this example is highly efficient to modify only one and only one working electrode.

Example 8

This example illustrates a schematic to produce an array of highly sensitive microelectrode devices that are independently addressed via an active matrix element. This device is composed of array of thin wires embedded at one edge within a flexible encasing and are electrically separated from each other by an insulating layer. Such array can be produced by fusing multiple insulated wires, where the insulation has filled all the gaps. Alternatively, glass coated wires are fused together or co-extruded to form arrays of desired size and density. These are then cut into a thin slice and polished on both sides to expose the edges of the said micron wires. One of the exposed edges are electrochemically etched to increase their surface area and subsequently coated with nano-sized electro-catalytic moieties suitable for the catalysis of a given redox species. The other exposed edges are connected to an active matrix (via flip-chip bonding, ultra sonic bonding, electropolymerization, conductive adhesives, soldering micro- or nanobeads, and the like) that is in turn connected to an appropriate microelectronics for signal detection. The active matrix is capable of switching and interrogating between different said thin wires and minimizes the number of interconnects within the device encasing.

The sensors disclosed herein can be advantageously used for the simultaneous and independent determination of metabolites in the body of a living being. These sensors are highly flexible and are miniaturized. The have a high electro-active area and display 3-dimensional analyte diffusion. They afford high enzyme loadings and permit high sensor performance and usability. They can be fabricated in a manner that permits them being rolled up for storage. They can be manufactured in a large scale roll-to-roll process. The biosensor is also capable of detecting analytes with a low applied potential. They display very low detection limits and display no interferences from endogenous species. They have a high signal to noise ratio.

In one embodiment, the sensor has a diameter of about 10 micrometers to about 1,000 micrometers, specifically about 20 micrometers to about 500 micrometers, and more specifically about 30 micrometers to about 250 micrometers. Having such a narrow diameter (or thickness in the case of the "tape" sensor) allows the shape of the sensor to be adjusted and readjusted if desired. In one embodiment, the sensor is flexible enough that its shape can be adjusted by hand without the use of any tools.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:
1. A sensor comprising:
a first tape;
a second tape; the second tape being opposedly disposed on the first tape and in contact with the first tape; and one or multiple working electrodes, one or multiple reference electrodes and one or multiple counter electrode, each being disposed between the first tape and the second tape; where the working, reference and counter electrode are continuous along the length of the first tape and the second tape;

the working, reference and counter electrodes not being in contact with one another; wherein a cross-sectional area of a first end of the sensor in a longitudinal direction that comprises a section of the working electrode, a section of the reference electrode and a section of the counter electrode is exposed to, contacts and detects analytes and a second end of the sensor in a longitudinal direction is not exposed to analytes;

the working electrodes are etched to increase their surface area and catalytic nanoparticles are directly disposed and activated onto the etched surfaces to afford increase electro catalytic activity against $H_2O_2$ sensing;

a thin film of permselective membrane is directly disposed onto said catalytic nanoparticles of the working electrodes to increase selectivity against $H_2O_2$ sensing, while retaining significant amount of the original nanoparticle sensitivity;

a variety of analyte specific enzymes is directly disposed onto said permselective membrane to render the working, reference and counter electrodes operative to detect a variety of analytes via an electrochemical oxidation or reduction reaction; and wherein an old section of the sensor that contacts the analyte can be severed off to expose a new section of the sensor to detect the analyte.

2. The sensor of claim 1, where the tape comprises a polyimide.

3. The sensor of claim 1, where the working electrode, the reference electrode and the counter electrode each comprise at least one metal selected from the group consisting of gold, silver, platinum, rhodium, iridium, palladium, copper, carbon fibers and combinations thereof.

4. The sensor of claim 1, where the working electrode is composed of gold and the catalytic nanoparticles directly disposed on it are composed of platinum.

5. The sensor of claim 1, where the thin film of permselective membrane directly disposed onto said catalytic nanoparticles is composed of electropolymerized flavin mononucleotide.

6. The sensor of claim 1, where the thin film of permselective membrane directly disposed onto said catalytic nanoparticles is composed of electropolymerized mixture of flavin mononucleotide and nanotubes.

7. The sensor of claim 1, where the thin film of permselective membrane directly disposed onto said catalytic nanoparticles is composed of electropolymerized mixture of flavin mononucleotide, nanotubes and conductive polymers comprised of at least one monomer selected from the group consisting of ortho-phenylene diamine (OPD), para-phenylene-diamine, meta-phenylene diamine, phenol, pyrrole, flavins, naphthalene, polyaniline, aniline, thiophenes, sulfonated aniline, sulfonated pyrrole and combinations thereof.

8. The sensor of claim 1, where the said analyte specific enzymes is composed of glucose oxidase.

9. The sensor of claim 1, where one or more working electrodes are left devoid of said analyte specific enzymes so that can act as background sensors.

10. The sensor of claim 9, where the background sensors are used to internally calibrate the sensors composed with said analyte specific enzymes by providing background currents.

11. The sensor of claim 1, where the said working electrodes, the said reference electrodes and the said counter electrodes each have a width of about 10 nanometers to about 100 micrometers.

* * * * *